(12) United States Patent
Huang et al.

(10) Patent No.: US 11,540,798 B2
(45) Date of Patent: Jan. 3, 2023

(54) DILATED CONVOLUTIONAL NEURAL NETWORK SYSTEM AND METHOD FOR POSITRON EMISSION TOMOGRAPHY (PET) IMAGE DENOISING

(71) Applicant: The Research Foundation for the State University of New York, Albany, NY (US)

(72) Inventors: Chuan Huang, East Setauket, NY (US); Karl Spuhler, Poughkeepsie, NY (US); Mario Serrano Sosa, Glen Cove, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 17/638,570

(22) PCT Filed: Aug. 28, 2020

(86) PCT No.: PCT/US2020/048347
§ 371 (c)(1),
(2) Date: Feb. 25, 2022

(87) PCT Pub. No.: WO2021/041772
PCT Pub. Date: Mar. 4, 2021

(65) Prior Publication Data
US 2022/0287671 A1 Sep. 15, 2022

Related U.S. Application Data

(60) Provisional application No. 62/893,964, filed on Aug. 30, 2019.

(51) Int. Cl.
*G06K 9/00* (2022.01)
*A61B 6/00* (2006.01)
(Continued)

(52) U.S. Cl.
CPC ............ *A61B 6/5258* (2013.01); *A61B 6/037* (2013.01); *A61B 6/5205* (2013.01); *G06N 3/08* (2013.01);
(Continued)

(58) Field of Classification Search
CPC ..... A61B 6/5258; A61B 6/037; A61B 6/5205; G06N 3/08; G06N 3/0481; G06N 3/0454;
(Continued)

(56) References Cited

U.S. PATENT DOCUMENTS 7,480,365 B1   1/2009   Topfer et al.
8,208,599 B2   6/2012   Ye et al.
(Continued)

FOREIGN PATENT DOCUMENTS

CN    106940895 A    7/2017
CN    107633486 A    1/2018
(Continued)

OTHER PUBLICATIONS

Umair Javaid, et al., "Multi-organ Segmentation of Chest CT Images in Radiation Oncology: Comparison of Standard and Dilated UNet", ACIVS 2018, LNCS 11182, pp. 188-199, 2018.
(Continued)

*Primary Examiner* — Charlotte M Baker
(74) *Attorney, Agent, or Firm* — Hoffmann & Baron, LLP

(57) ABSTRACT

A method for performing positron emission tomography (PET) image denoising using a dilated convolutional neural network system includes: obtaining, as an input to the dilated convolutional neural network system, a noisy image; performing image normalization to generate normalized image data corresponding to the noisy image; encoding the normalized image data using one or more convolutions in the dilated convolutional neural network, whereby a dilation rate is increased for each encoding convolution performed to
(Continued)

generate encoded image data; decoding the encoded image data using one or more convolutions in the dilated convolutional neural network, whereby dilation rate is decreased for each decoding convolution performed to generate decoded image data; synthesizing the decoded image data to construct a denoised output image corresponding to the noisy image; and displaying the denoised output image on an image display device, the denoised output image having enhanced image quality compared to the noisy image.

19 Claims, 11 Drawing Sheets

(51) Int. Cl.
  A61B 6/03  (2006.01)
  G06N 3/08  (2006.01)
  G06T 3/60  (2006.01)
  G06T 5/00  (2006.01)
  G06T 9/00  (2006.01)

(52) U.S. Cl.
  CPC ............... *G06T 3/60* (2013.01); *G06T 5/002* (2013.01); *G06T 9/002* (2013.01); *G06T 2207/10104* (2013.01); *G06T 2207/20081* (2013.01); *G06T 2207/20084* (2013.01); *G06T 2207/30016* (2013.01)

(58) Field of Classification Search
  CPC ........... G06T 3/60; G06T 5/002; G06T 9/002; G06T 2207/10104; G06T 2207/20081; G06T 2207/20084; G06T 2207/30016; G06T 2207/20016; G06T 5/20
  USPC ........................................................ 382/131
  See application file for complete search history.

(56) References Cited

U.S. PATENT DOCUMENTS

| | | | |
|---|---|---|---|
| 10,426,442 B1 | 10/2019 | Schnorr | |
| 10,646,156 B1* | 5/2020 | Schnorr ............... | G06N 3/0454 |
| 10,796,414 B2 | 10/2020 | Vogels et al. | |
| 11,120,582 B2 | 9/2021 | Zhou et al. | |
| 11,223,833 B2 | 1/2022 | Andreopoulos et al. | |
| 11,263,782 B2 | 3/2022 | Hwang et al. | |
| 11,315,221 B2 | 4/2022 | Matsuura et al. | |
| 11,398,016 B2 | 7/2022 | Meng et al. | |
| 2005/0129170 A1 | 6/2005 | Watson et al. | |
| 2012/0106817 A1 | 5/2012 | Shih et al. | |
| 2018/0068463 A1 | 3/2018 | Risser | |
| 2019/0005603 A1 | 1/2019 | Chen et al. | |
| 2019/0050999 A1 | 2/2019 | Piat et al. | |
| 2019/0066346 A1 | 2/2019 | Ye et al. | |
| 2019/0095795 A1 | 3/2019 | Ren et al. | |
| 2019/0104940 A1 | 4/2019 | Zhou et al. | |
| 2019/0108904 A1 | 4/2019 | Zhou et al. | |
| 2019/0213761 A1 | 7/2019 | Rosen et al. | |
| 2019/0251668 A1 | 8/2019 | Meyer et al. | |
| 2019/0318726 A1 | 10/2019 | Jin et al. | |
| 2020/0027198 A1 | 1/2020 | Vogels et al. | |
| 2020/0034948 A1 | 1/2020 | Park et al. | |
| 2020/0104711 A1 | 4/2020 | Aytekin et al. | |
| 2020/0126191 A1 | 4/2020 | Munkberg et al. | |
| 2020/0126192 A1 | 4/2020 | Munkberg et al. | |
| 2020/0184605 A1 | 6/2020 | Vogels et al. | |
| 2020/0242739 A1 | 7/2020 | Laine et al. | |
| 2020/0311878 A1 | 10/2020 | Matsuura et al. | |
| 2021/0074036 A1 | 3/2021 | Fuchs et al. | |
| 2021/0118098 A1 | 4/2021 | Chan et al. | |
| 2021/0118099 A1 | 4/2021 | Kearney et al. | |
| 2021/0256657 A1 | 8/2021 | Meng | |
| 2021/0272246 A1 | 9/2021 | Meng et al. | |
| 2021/0287342 A1 | 9/2021 | Yang et al. | |
| 2021/0312591 A1 | 10/2021 | Ren et al. | |
| 2021/0366169 A1 | 11/2021 | Liu et al. | |
| 2022/0036523 A1 | 2/2022 | Moran et al. | |
| 2022/0107378 A1 | 4/2022 | Dey et al. | |
| 2022/0108466 A1* | 4/2022 | Mendlovic ........... | G06N 3/0454 |
| 2022/0138910 A1 | 5/2022 | Serra Lleti | |
| 2022/0188602 A1 | 6/2022 | Meyer et al. | |
| 2022/0207651 A1 | 6/2022 | Meng et al. | |
| 2022/0207870 A1 | 6/2022 | Meng et al. | |

FOREIGN PATENT DOCUMENTS

| | | |
|---|---|---|
| CN | 107871306 A | 4/2018 |
| CN | 109389556 A | 2/2019 |
| CN | 109584246 A | 4/2019 |
| CN | 109671026 A | 4/2019 |
| CN | 109727211 A | 5/2019 |
| CN | 109754376 A | 5/2019 |
| CN | 110097512 A | 8/2019 |
| CN | 110298804 A | 10/2019 |
| CN | 110310244 A | 10/2019 |
| CN | 110619607 A | 12/2019 |
| CN | 110706181 A | 1/2020 |
| CN | 110728627 A | 1/2020 |
| CN | 110852961 A | 2/2020 |
| CN | 111028163 A | 4/2020 |
| CN | 111127336 A | 5/2020 |
| CN | 111242862 A | 6/2020 |
| CN | 111583135 A | 8/2020 |
| CN | 111882503 A | 11/2020 |
| CN | 112085677 A | 12/2020 |
| CN | 112233038 A | 1/2021 |
| CN | 112351739 A | 2/2021 |
| CN | 112381741 A | 2/2021 |
| CN | 112396560 A | 2/2021 |
| CN | 112651890 A | 4/2021 |
| CN | 112801906 A | 5/2021 |
| CN | 112819732 A | 5/2021 |
| CN | 112967195 A | 6/2021 |
| CN | 112991203 A | 6/2021 |
| CN | 113327205 A | 8/2021 |
| CN | 113344799 A | 9/2021 |
| CN | 113379613 A | 9/2021 |
| CN | 113396440 A | 9/2021 |
| CN | 113476064 A | 10/2021 |
| CN | 113487528 A | 10/2021 |
| CN | 113674159 A | 11/2021 |
| CN | 113723255 A | 11/2021 |
| CN | 113763292 A | 12/2021 |
| CN | 113837959 A | 12/2021 |
| CN | 113888405 A | 1/2022 |
| CN | 114529463 A | 5/2022 |
| EP | 3509013 A1 | 7/2019 |
| EP | 3576049 A2 | 12/2019 |
| EP | 3470006 B1 | 6/2020 |
| EP | 3751513 A1 | 12/2020 |
| EP | 3846475 A1 | 7/2021 |
| EP | 4009268 A1 | 6/2022 |
| JP | 2019211475 A | 12/2019 |
| JP | 2020064609 A | 4/2020 |
| JP | 2020517946 A | 6/2020 |
| JP | 2020168353 A | 10/2020 |
| JP | 2021013725 A | 2/2021 |
| KR | 20190204636 A | 3/2019 |
| KR | 102089151 B1 | 3/2020 |
| KR | 20210089166 A | 7/2021 |
| WO | 2017223560 A1 | 12/2017 |
| WO | 2018200493 A1 | 11/2018 |
| WO | 2020048359 A1 | 3/2020 |
| WO | 2020070387 A1 | 4/2020 |
| WO | 2020128134 A1 | 6/2020 |
| WO | 2020177607 A1 | 9/2020 |
| WO | 2020219915 A1 | 10/2020 |
| WO | 2020240468 A1 | 12/2020 |
| WO | 2021041125 A1 | 3/2021 |
| WO | 2021041772 A1 | 3/2021 |
| WO | 2021062413 A1 | 4/2021 |
| WO | 2021063118 A1 | 4/2021 |
| WO | 2021063119 A1 | 4/2021 |

(56) References Cited

FOREIGN PATENT DOCUMENTS

| WO | 2021067186 A2 | 4/2021 |
|---|---|---|
| WO | 2021110262 A1 | 6/2021 |
| WO | 2021226862 A1 | 11/2021 |
| WO | 2021230708 A1 | 11/2021 |
| WO | 2021232653 A1 | 11/2021 |
| WO | 2021233767 A1 | 11/2021 |
| WO | 2022008363 A1 | 1/2022 |
| WO | 2022017738 A1 | 1/2022 |
| WO | 2022027216 A1 | 2/2022 |
| WO | 2022047625 A1 | 3/2022 |
| WO | 2022126588 A1 | 6/2022 |

OTHER PUBLICATIONS

Umair Javaid, et al., "Semantic Segmentation of Computed Tomography for Radiotherapy with Deep Learning: Compensating Insufficient Annotation Quality Using Contour Augmentation", Proc. SPIE 10949, Medical Imaging 2019: Image Processing, 109492P (Mar. 15, 2019); doi: 10.1117/12.2512461, pp. 1-14.

Yuhong Li, et al., "CSRNet: Dilated Convolutional Neural Networks for Understanding the Highly Congested Scenes," arXiv:1802.10062v4 [cs.CV] pp. 1-16; Apr. 11, 2018.

Wei Zhang, et al., "A Robust Iris Segmentation Scheme Based on Improved U-Net", IEEE Access, vol. 7, pp. 1-8, Jul. 15, 2019.

Anna M. Dnkla, et al., "MR-Only Brain Radiation Therapy: Dosimetric Evaluation of Synthetic CTs Generated by a Dilated Convolutional Neural Network," Int J. Radiation Oncol Biol. Phys., vol. 102, No. 4, pp. 801-812, 2018.

Sachin Mehta, et al., "ESPNetv2: A Light-weight, Power Efficient, and General Purpose Convolutional Neural Network", arXiv:1811.11431v3 [cs.CV], pp. 1-11, Mar. 30, 2019.

Lichen Zhou, et al., "D-LinkNet: LinkNet with Pretrained Encoder and Dilated Convolution for High Resolution Satellite Imagery Road Extraction," 2018 IEEE/CVF Conference on Computer Vision and Pattern Recognition Workshops (CVPRW), 2018, pp. 182-186, doi: 10.1109/CVPRW.2018.00034.

Baixiang Zhao, et al., "Segmentation of Head and Neck Tumours Using Modified U-net," 2019 27th European Signal Processing Conference (EUSIPCO), 2019, pp. 1-4, doi: 10.23919/EUSIPCO.2019.8902637.

Liyan Sun, et al., "Compressed Sensing MRI Using a Recursive Dilated Network," AAAI'18: AAAI Conference on Artificial Intelligence, Article No. 298, Feb. 2018, pp. 2444-2451.

Chengjia Wang, et al., "A two-Stage 3D Unet Framework for Multi-Class Segmentation on Full Resolution Image", BHF Centre of Cardiovascular Science and MICCAI 2017 Multi-Modality Whole Heart Segmentation; arXiv:1804.04341v1 [cs.CV], pp. 1-10, Apr. 12, 2018.

Fisher Yu, et al., "Dilated Residual Networks," CVR, pp. 472-480.

Junshen Xu, et al., "200x Low-dose PET Reconstruction Using Deep Learning," arXiv:1712.04119v1 [cs.CV], pp. 1-9, Dec. 12, 2017.

Harshall Lamba, "Understanding Semantic Segmentation with UNET, " Towards Data Science, pp. 1-28, Feb. 17, 2019.

* cited by examiner

DILATED CONVOLUTIONAL NEURAL NETWORK SYSTEM AND METHOD FOR POSITRON EMISSION TOMOGRAPHY (PET) IMAGE DENOISING

CROSS-REFERENCE TO RELATED APPLICATIONS

This application is the U.S. national phase application of international application no. PCT/US2020/048347 filed on 28 Aug. 2020, which claims priority to provisional application No. 62/893,964 filed on 30 Aug. 2019, entitled "Dilated Convolutional Neural Network System and Method for PET Denoising Using Same," the disclosures of which are incorporated by reference herein in their entirety for all purposes.

BACKGROUND

The present invention relates generally to the electrical, electronic and computer arts, and, more particularly, relates to enhanced positron emission tomography (PET).

Positron emission tomography (PET), also called PET imaging or a PET scan, is a type of nuclear medicine imaging that uses small amounts of radioactive material called radiotracers or radiopharmaceuticals to diagnose, evaluate or treat a variety of diseases. By identifying changes at the cellular level, PET may detect the early onset of disease before other imaging tests can. PET may also show whether a patient is responding to treatment.

PET provides clinicians with a highly sensitive functional imaging tool to investigate a range of pathologies, such as cancer, heart disease and brain disorders, and is an integral part of contemporary cancer diagnosis and treatment. However, various physical degradation factors limit the number of detected photons, resulting in poor image resolution and signal-to-noise ratio (SNR). High SNR in PET images is advantageous for applications such as detection of small lesions and early diagnosis of neurological disease. In order to obtain images with high SNR for diagnostic or research use, the scanner must register a large number of radioactive decay events. As such, attaining high SNR generally comes at the cost of either relatively high radiation dose and/or long scan time. Higher radiation dose can lead to greater risk of stochastic effects, such as greater lifetime risk of cancer. Similarly, longer acquisition times require subjects to remain still for an extended period of time, which increases the likelihood of subject motion that can degrade image quality. Although lowering radiation dose or decreasing scan time would reduce negative impacts on the patient, current reconstruction methods would result in images with unacceptable quality for diagnostic purposes.

SUMMARY

The present invention, as manifested in one or more embodiments thereof, is directed to methods and apparatus for providing a low-count PET image denoising pipeline configured to decrease subject burden without sacrificing image quality. Deep learning techniques have received much attention in the area of image denoising. However, substantial differences arise in the various types of deep learning methods dealing with image denoising. Specifically, discriminative learning based on deep learning may address the issue of Gaussian noise. Furthermore, optimization models based on deep learning may be effective in estimating real noise. There has thus far been little related research relating to deep learning techniques for image denoising.

In accordance with an embodiment of the invention, a method is provided for performing PET image denoising using a dilated convolutional neural network system. The method includes: obtaining, as an input to the dilated convolutional neural network system, a noisy image; performing image normalization to generate normalized image data corresponding to the noisy image; encoding the normalized image data using one or more convolutions in the dilated convolutional neural network, whereby a dilation rate is increased for each encoding convolution performed to generate encoded image data; decoding the encoded image data using one or more convolutions in the dilated convolutional neural network, whereby dilation rate is decreased for each decoding convolution performed to generate decoded image data; synthesizing the decoded image data to construct a denoised output image corresponding to the noisy image; and displaying the denoised output image on an image display device, the denoised output image having enhanced image quality compared to the noisy image.

In accordance with another embodiment of the invention, an apparatus is provided for performing PET image denoising using a dilated convolutional neural network system. The apparatus includes memory and at least one processor coupled to the memory, the processor implementing a dilated convolutional neural network and being configured: to obtain, as an input to the dilated convolutional neural network, a noisy image; to perform image normalization on the noisy image to generate normalized image data corresponding to the noisy image; to encode the normalized image data using one or more convolutions in the dilated convolutional neural network, whereby a dilation rate is increased for each encoding convolution performed to generate encoded image data; to decode the encoded image data using one or more convolutions in the dilated convolutional neural network, whereby dilation rate is decreased for each decoding convolution performed to generate decoded image data; to synthesize the decoded image data to construct a denoised output image corresponding to the noisy image; and to display the denoised output image on an image display device, the denoised output image having enhanced image quality compared to the noisy image.

In accordance with yet another embodiment, a computer program product is provided. The computer program product includes a non-transitory computer readable storage medium having computer readable program code embodied thereon for performing PET image denoising. The computer readable program code, when executed on at least one processor, causes the processor: to obtain, as an input to the dilated convolutional neural network, a noisy image; to perform image normalization on the noisy image to generate normalized image data corresponding to the noisy image; to encode the normalized image data using one or more convolutions in the dilated convolutional neural network, whereby a dilation rate is increased for each encoding convolution performed to generate encoded image data; to decode the encoded image data using one or more convolutions in the dilated convolutional neural network, whereby dilation rate is decreased for each decoding convolution performed to generate decoded image data; to synthesize the decoded image data to construct a denoised output image corresponding to the noisy image; and to display the denoised output image on an image display device, the denoised output image having enhanced image quality compared to the noisy image.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof may be implemented in the form of a computer program product including a non-transitory computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques as disclosed herein can provide substantial beneficial technical effects. By way of example only and without limitation, one or more embodiments of the invention may provide one or more of the following advantages:
- achieves improved SNR of low-count PET brain images;
- provide techniques for predicting full-count images by introducing a dilated convolutional neural network architecture (dNet) inspired by a U-Net architecture;
- improves upon U-Net performance, not only for static, but also for dynamic PET image analysis;
- exploits the exponentially expanding nature of dilated convolutions, applied in the context of image processing, to avoid down-sampling and up-sampling images and thereby conserve resolution in a PET image denoising task.

These and other features and advantages will become apparent from the following detailed description of illustrative embodiments thereof, which is to be read in connection with the accompanying drawings.

BRIEF DESCRIPTION OF THE DRAWINGS

Non-limiting and non-exhaustive embodiments of the present invention will be described with reference to the following drawings which are presented by way of example only, wherein like reference numerals (when used) indicate corresponding elements throughout the several views unless otherwise specified, and wherein.

Figure 1A:
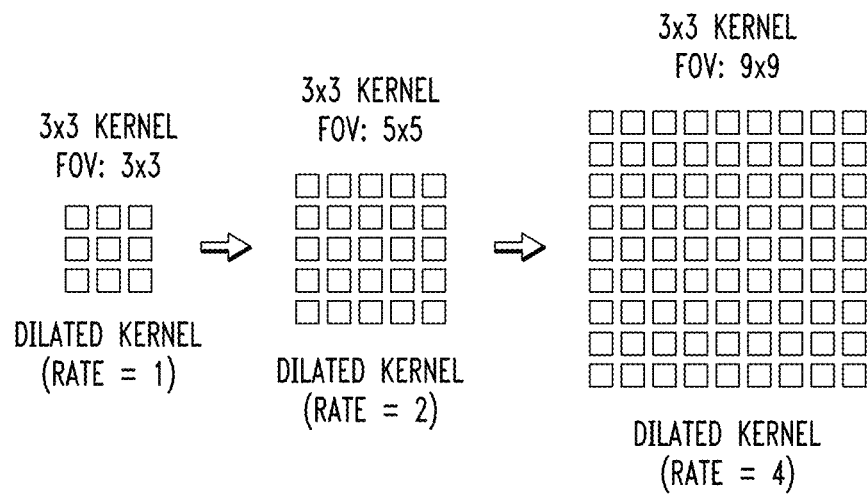
FIGS. 1A and 1B conceptually depict exemplary dilated convolution kernels used in a dilated convolutional neural network architecture (dNet), according to an embodiment of the present invention.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Principles of the present disclosure will be described herein in the context of an illustrative dilated convolutional neural network system and methods for positron emission tomography (PET) denoising. One or more embodiments of the invention provide a synergistic union of dilated convolutional neural networks and U-Net for an end-to-end trainable framework for low-count PET image denoising. The system and methods according to aspects of the invention outperforms U-Net and also shows better edge preservation, as demonstrated by improved peak signal-to-noise ratio (SNR) and structural similarity index metrics. It is to be appreciated, however, that the specific methods and/or apparatus illustratively shown and described herein are to be considered exemplary as opposed to limiting. Moreover, it will become apparent to those skilled in the art given the teachings herein that numerous modifications can be made to the embodiments shown that are within the scope of the appended claims. That is, no limitations with respect to the embodiments shown and described herein are intended or should be inferred.

For a number of reasons, including the amount of radiation and time required for quantitatively accurate scanning, methods for accurately reconstructing low-count PET data are desirable. Many handcrafted pipelines have been developed for this, but recently the convolutional neural network (CNN) has offered the potential of a fully data-driven paradigm for low-count PET image denoising. Recent work showed results for a familiar CNN known as U-Net in this task. One of the main attractive features of CNN in this use case is the potential for small feature and edge preservation, a common limitation of conventional image denoising algorithms.

One or more embodiments of the invention described herein provides a novel framework which incorporates atrous or dilated convolutions to enhance image structure-preserving properties. In comparison to U-Net, the framework according to embodiments of the invention significantly outperforms U-Net, particularly when recapitulating high-count PET data from low-count corruptions. Embodiments of the invention offer this improvement, in one or more aspects, by obviating the need to down-sample hidden layer image representations, which must be subsequently up-sampled at the cost of edge quality through the use of the dilated convolution.

The system and method described herein has advantages over a conventional U-Net approach for low-count PET denoising in terms of objective image quality metrics. (See, e.g., Junshen Xu, et al., "200× Low-dose PET Reconstruction Using Deep Learning," https://arxiv.org/pdf/1712.04119.pdf, which is incorporated by reference herein in its entirety for all purposes). Specifically, the system and method according to embodiments of the invention beneficially improves upon U-Net performance, not only for static, but also for dynamic PET image analysis.

Software advances have been introduced that can easily be incorporated into clinical workflow. Specifically, three distinct software methods that have been developed for improving the quality of PET images are iterative reconstruction algorithms, post-reconstruction image filtering and various machine learning methods. Iterative reconstruction methods have the desirable trait of operating with raw emission data. In general, these algorithms treat low dose PET reconstruction as an optimization problem, where the goal is to estimate an image that would most likely lead to the raw data observed by the scanner. In addition to this, some manner of regularization is added to the image reconstruction objective to penalize noise properties. For example, iterative PET reconstruction algorithms have been augmented with a total variation regularizer, which seeks to enforce smoothness in the image space. Despite the ideality of working in the raw data domain, iterative reconstruction algorithms suffer from increased computational time and are dependent upon many parameters that currently lack a principled method for selection.

Post-reconstruction methods that use image filtering or sparse methods to predict standard-dose PET from low-dose PET have also succeeded in denoising PET images. Common image filtering techniques such as nonlocal means and block matching are well established in the field. Despite achieving higher visual quality, these methods tend to undesirably rely on a large number of parameters that are yet to be standardized.

Across all image denoising methods, proper assessment has been standardized for comparing the proposed method to ground truth. These assessments are typically done through the use of objective (i.e., quantitative assessment) and/or subjective (i.e., visual interpretation) measures, with the prior being more robust and thus preferred. Objective measures typically include, but are not limited to, mean absolute percent error (MAPE), peak signal to noise ratio (PSNR) and structural similarity index metric (SSIM). MAPE is a metric that distinguishes voxel-wise differences between ground truth and the proposed model; smaller differences in MAPE shows improvement in denoising method. PSNR is a metric that measures the power of signal and power of corrupting noise; larger PSNR represents the quality of suppressing noise in the denoising method. SSIM measures how well the proposed denoising method recovered structure and edge compared to the ground truth image; higher SSIM indicates a reduction in image dissimilarity with the denoising method. By contrast, subjective analysis uses visual interpretation of perceived image quality and the relative preservation of detail and edges to assess the performance of the image denoising method.

Recently, machine learning methods for PET denoising have emerged and shown improvement in both objective and subjective assessment. As described in Wang et al., "Predicting Standard-Dose PET Image from Low-Dose PET and Multimodal MR Images Using Mapping-Based Sparse Representation," *Physics in Medicine & Biology*, 2016, 61(2), p. 791, the disclosure of which is incorporated by reference herein, using a supervised dictionary-based method, Wang et. al successfully reduced dose by a factor of four with comparable image quality, as assessed by objective and subjective measures, to full-count PET. Other methods using a modest CNN architecture demonstrated increased PSNR compared to sparse-learning based procedures for recovering standard dose PET images. Most strikingly, a publication proposed a residual U-Net architecture which can reliably estimate standard dose PET data from low-dose scans with a dose reduction factor as high as 200. Other machine learning frameworks have used multi-modal CNNs and end-to-end CNN reconstruction methods to estimate full-count PET from low-count PET.

In Chen et al., "Ultra-Low Dose 18F-Florbetaben Amyloid PET Imaging Using Deep Learning with Multi-Contrast MRI Inputs," *Radiology*, 2019, 290(3), pp. 649-656, the disclosure of which is incorporated by reference herein, Chen et. al. used inputs of two-dimensional (2D) PET slices with various 2D MRI contrasts—such as T1, T2 and DWI—into a U-Net architecture to output full-dose PET images. Although their results were successful in denoising the low-count image, development of a multi-modality method to denoise PET images is restrictive in accomplishing a generalizable PET denoising method to be used across different scanners. Likewise, Chen's group used [$^{18}$F]-Florbetaben and a subjective scale for a binary (positive/negative) clinical evaluation task. Being a binary task, high resolution was not critical; therefore, the task was not sensitive to blurring, resolution, integrity of fine structure and edges. As described in Haggstrom et. al., "DeepPET: A Deep Encoder-Decoder Network for Directly Solving the PET Image Reconstruction Inverse Problem," *Medical Image Analysis*, 2019, 54, pp. 253-262, the disclosure of which is incorporated by reference herein, Haggstrom et. al. developed a deep encoder-decoder network for low-count PET reconstruction. This work utilized simulated data and input sinograms into their network to output their simulated full-count PET image.

A majority of studies have adopted the well-established U-Net architecture. Typically, U-Net architectures down-sample and up-sample feature maps as they are fed into the network, which undesirably degrades resolution and fine details. Notably, U-Net processing introduces some degree of blurring from two primary sources. The first source of blurring is the mathematical nature of the convolution. Secondly, the common practice of down-sampling and subsequently up-sampling feature maps as they pass through the network also adds a degree of blurring. Dilated kernels are a method to avoid down-sampling layers and subsequent up-sampling layers that typically degrade resolution by expanding the kernel itself to increase the receptive field size.

Embodiments of the invention beneficially achieve improved SNR of low-count PET brain images and provide techniques for predicting full-count images by introducing a dilated convolutional neural network architecture (dNet) inspired by the U-Net architecture. The dNet according to one or more embodiments of the invention uses dilated kernels to convolve with the feature maps in order to preserve resolution while simultaneously growing field of view to observe larger and more unique features. That is, embodiments of the invention utilize dilated convolutions for image segmentation, wherein the dilated kernels enlarge the field-of-view to incorporate multiscale context. In one or more embodiments, residual learning is integrated into the architecture to capture the desired mapping of low-count to full-count images and enhance convergence.

By way of example only and without limitation, a model according to aspects of the invention was implemented and evaluated on $^{18}$F-FDG PET images of the brain with images reconstructed with $\frac{1}{10}^{th}$ counts as input and original full-count images as output. The dilated convolution was originally introduced as a method to exponentially increase neuron receptive field size in a memory-efficient manner. This paradigm may allow a user to construct a novel multiscale dilated CNN approach which synthesizes more quantitatively accurate full-count PET estimates than the standard U-Net, as reflected by improved MAPE, PSNR and SSIM.

Figure 1B:
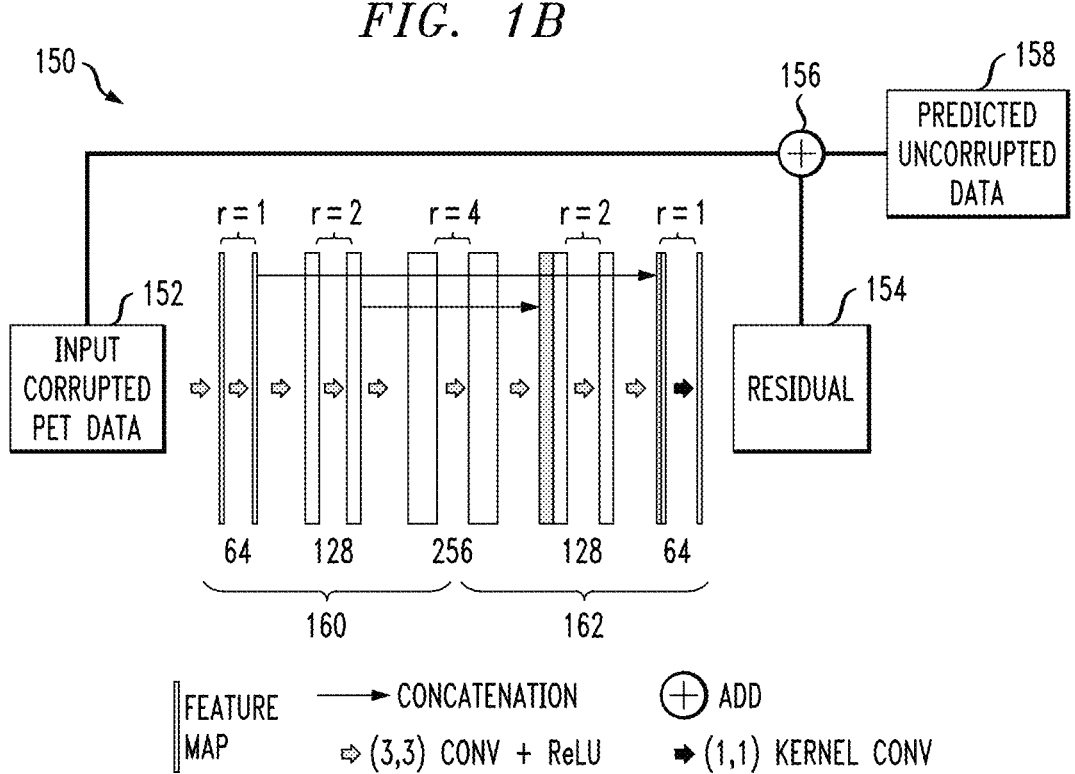

FIGS. 1A and 1B conceptually depict exemplary dilated convolution kernels used in dNet, according to an embodiment of the invention. The dilated convolution introduces a dilation factor to the standard convolution to define the amount of zero-padding placed between learnable elements of the filter. One or more embodiments of the invention provide two deep learning models for comparison of PET image denoising: a conventional U-Net model and a dNet model according to aspects of the invention. Both models were trained on 35 subjects with leave-one out cross-validation. For non-CNN based denoising methods, a three-dimensional (3D) 5 millimeter (mm) full-width at half maximum (FWHM) Gaussian filtering method was applied and compared to both CNN models. Comparison of these three models was evaluated through objective imaging metrics: peak signal-to-noise ratio (PSNR), structural similarity index metric (SSIM), and mean absolute percent error (MAPE). Furthermore, region of interest (ROI) uptake was analyzed with both CNN models. Both deep learning models incorporated a residual learning approach, with the networks being trained to represent the full-count image as the sum of the low-count image and a learned network representation.

More particularly, dilated convolutions were developed to improve segmentation tasks. These dilated kernels are conceptually illustrated in FIG. 1A. With reference to FIG. 1A, each operation can be represented using only nine learnable weights, but cover exponentially larger receptive fields given a linear increase in dilation rate. This dilation allows for enlarging the filed-of-view without increasing the number of parameters of the amount of computation and can potentially observe larger scaled features compared to typical static kernels. Dilated convolutions with rate r introduces r−1 zeros between consecutive filter values, effectively enlarging the kernel size of a k×k filter to $k_e \times k_e$, where $k_e = k+(k-1)(r-1)$, where k and r are integers greater than or equal to one. This compromises the network to learn from both accurate localization (small field-of-view) and context assimilation (large field-of-view), which is desirable. Inclusion of upsampling and skip connections to concatenate corresponding contracting and expanding paths have been attempted in an effort to supplement this loss of localization accuracy and resolution.

Although these two processes (upsampling and skip connections) were added to preserve resolution, it is generally a supplement that is dynamically changing resolution, compared to the dNet approach according to embodiments of the invention, which does not change resolution. Therefore, by not changing the resolution throughout network propagation, it is expected that aspects of the invention will reduce noise and/or boost SNR. Embodiments of the invention beneficially exploit the exponentially expanding nature of dilated convolutions, applied in the context of image processing, to avoid down-sampling and up-sampling images and thereby conserve resolution in a PET image denoising task.

FIG. 1B conceptually depicts at least a portion of an exemplary dilated convolutional neural network 150 with residual learning, according to an embodiment of the invention. The dilated convolutional neural network 150 includes an input module or block 152 providing corrupted PET data, a residual learning module 154 configured to enhance convergence by capturing the desired mapping from corrupted to uncorrupted PET data without the need of a direct fit, and an adder 156 configured to sum the corrupted PET data from the input module 152 with residual function data generated by the residual learning module 154 to generate predicted uncorrupted PET data 158 as an output of the network 150. As apparent from FIG. 1B, the illustrative network 150 according to one or more embodiments of the invention employs a system of changing dilated convolutions in various rates r, from r=1, 2 and 4. This systemic approach was optionally taken primarily to resemble U-Net's feature map resolution increasing and decreasing in multiples of two due to max pooling and upsampling. It is to be appreciated, however, that embodiments of the invention are not limited to the specific rates shown.

Figure 2:
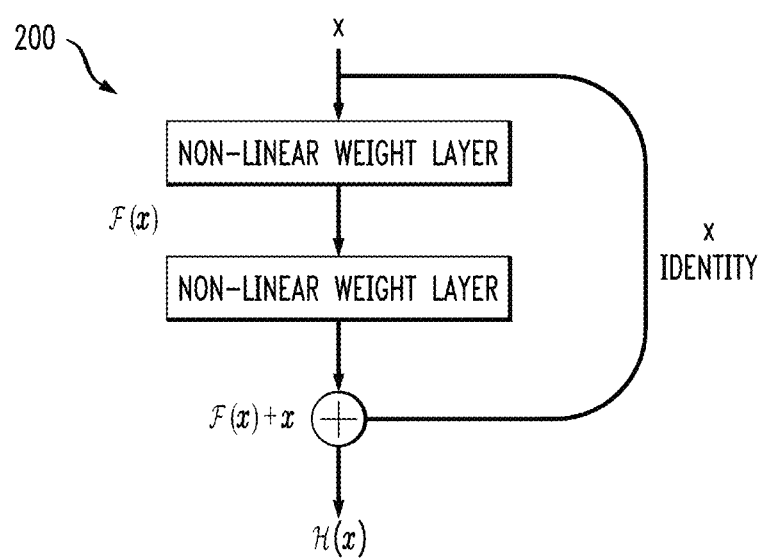
FIG. 2 is a block diagram conceptually depicting an exemplary residual learning block, where identity mapping is performed by adding the inputs with the outputs of stacked nonlinear weight layers.

Residual learning has been utilized to optimize image recognition by avoiding a direct fit to a desired mapping, but rather letting the layers fit a residual map. The basis of residual learning is that if multiple nonlinear layers can approximate complicated functions to the desired underlying mapping defined as $\mathcal{H}(x)$, the stacked nonlinear layers can also fit another mapping of $\mathcal{F}(x) = \mathcal{H}(x) - x$. This mapping is the approximation of a residual function (assuming input and output are of the same dimensions). The network mapping can be recast into $\mathcal{F}(x) + x$. FIG. 2 is a block diagram conceptually depicting an exemplary residual learning block 200, where identity mapping is performed by adding inputs with outputs of one or more stacked (i.e., consecutive) nonlinear weight layers. This residual mapping has been widely accepted and utilized in deep learning and is hypothesized to be optimal in converging image recognition tasks since it is easier to push a residual to zero than to fit an identity mapping by a stack of nonlinear layers.

The dNet architecture according to one or more embodiments of the invention is inspired by U-Net with similar multiscale hierarchical structure. With continued reference to FIG. 1B, 2D images are fed into dNet (e.g., input module 152) that is composed of convolutional blocks with five channel dimensions but different N feature channels between convolutional blocks; N feature channels are doubled in an "encoder" path 160 and halved in a "decoder" path 162. This illustrative embodiment includes five convolutional blocks, in which each block has two 3×3 kernel-convolutional layers followed by a rectified linear unit (ReLU) activation for a total of ten convolutional layers. Feature maps increase in a similar fashion as U-Net, as seen in FIG. 1B. U-Net feature maps contain max pooling functions and transpose convolutions in their encoder and decoder paths, respectively. As shown in FIG. 1B, dNet applies an increased or decreased dilation factor in each block of convolutions. This ultimately preserves resolution of the image across the entire path of the network. Furthermore, the decoder path 162 of dNet utilizes skip connections as originally employed in U-Net.

Figure 3:
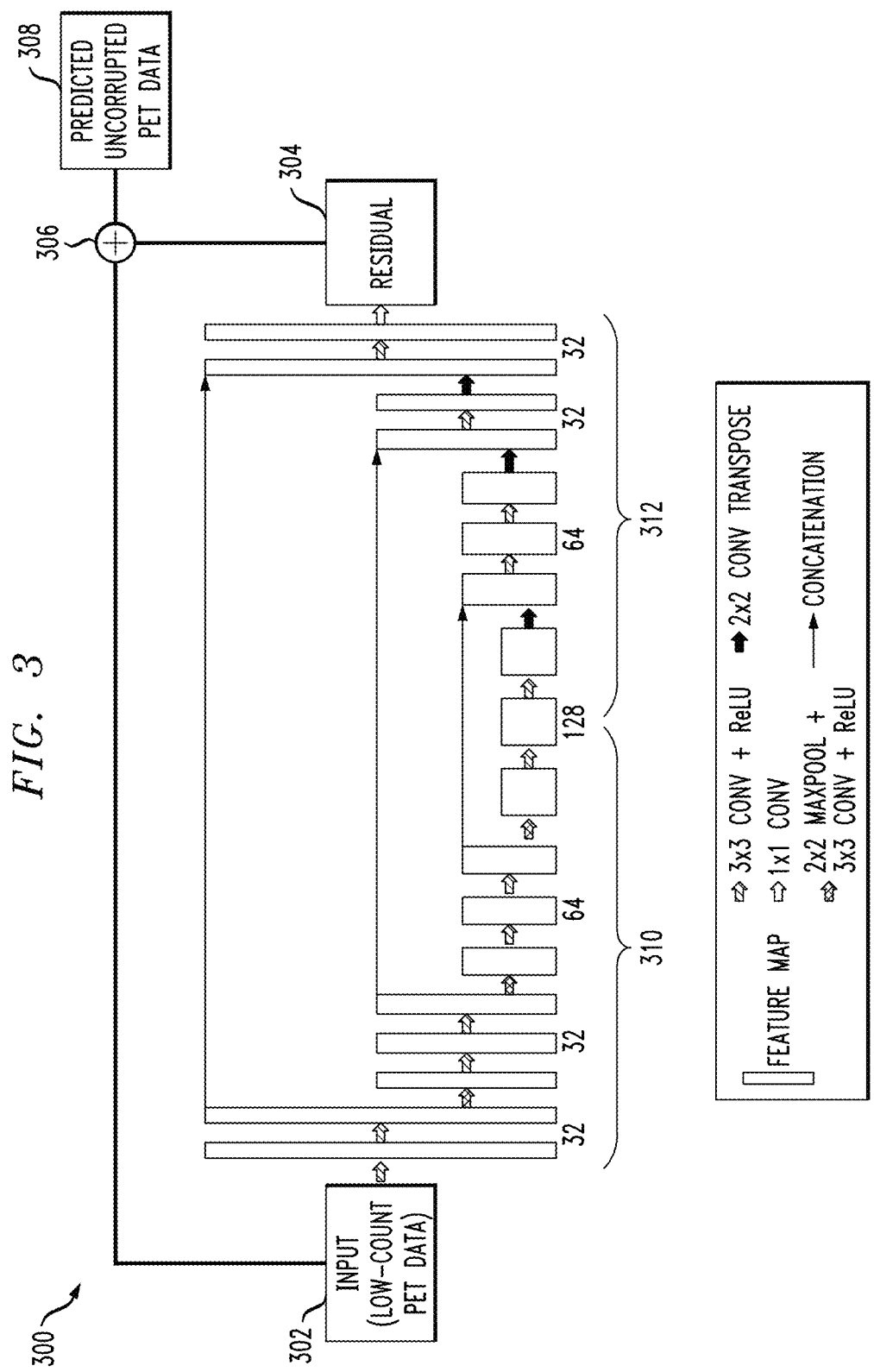
FIG. 3 conceptually depicts at least a portion of an exemplary residual U-Net architecture, according to an embodiment of the present invention.

To determine whether the dNet architecture in accordance with embodiments of the invention outperforms the established U-Net architecture, a conventional residual U-Net with network architecture as shown in FIG. 2 was trained. By way of example only and without limitation, FIG. 3 conceptually depicts at least a portion of an exemplary residual U-Net architecture 300, according to an embodiment of the invention. The U-Net architecture 300 comprises an input module 302, providing low-count PET data, and a residual learning module 304, providing training data. The data generated by the input module 302 and the residual learning module 304 are summed using an adder 306 to generate predicted uncorrupted PET data 308 as an output of the U-Net architecture 300.

The illustrative U-Net architecture 300 includes an encoding path (contracting, left side) 310 and a decoding path (expanding, right side) 312. The encoding path 310 conforms to the typical architecture of a CNN, including a repeated application of 3×3 convolution layers, each followed by a ReLU. Each block ends with a 2×2 max pooling layer for down-sampling followed by another 3×3 convolution layer plus ReLU. In addition, at each down-sampling stage (i.e., step), the number of feature channels is doubled in the encoding path 310. The decoding path 312 comprises a 2×2 transpose convolutional layer for upsampling. In this decoding path 312, the feature channel is halved and skip connections with the corresponding linked feature map from the encoding path 310 are utilized. The final stage/step is a 1×1 convolution that maps an output residual to the residual learning module 304.

For comparison purposes, both U-Net and dNet models were trained using residual learning. Training for both networks was very similar given their common architectures and purposes. Both networks employed an L1 loss function, as it has been shown that an L1 loss function encourages less blurring and sharper image outputs compared to an L2 loss function. As will be known by those skilled in the art, an L1 loss function is used to minimize the error which is a sum of all the absolute values of differences between a true value and a predicted value. An L1 loss function can be defined according the following expression:

$$f_{L1\ loss}(y) = \Sigma_{i=1}^{n} |y_{true} - y_{predicted}|$$

An L2 loss function is used to minimize the error which is a sum of all the squared differences between the true value and the predicted value. An L2 loss function can be defined according the following expression:

$$f_{L2\ loss}(y) = \Sigma_{i=1}^{n} (y_{true} - y_{predicted})^2$$

In the comparison example, both models had five channels and were trained using a 2.5D scheme to afford the network a degree of 3D information, where 3D slabs consisting of 5 slices were fed into the network, with slices comprising the channel dimension. These slabs contained the slice of interest (middle slice) along with two superior and two inferior slices. Both models were trained using an Adam optimizer and a non-decaying learning rate of $1 \times 10^{-5}$ with network parameters initialized using Glorot (also known as Xavier) Initialization. All convolutional kernel sizes contained 9 trainable elements initialized as 3×3 blocks, with dNet systematically changing the dilation rate at every convolutional block. All convolutional layers other than the output layer of each network employed batch normalization. The two networks were trained for 200 epochs to provide adequate time for the network to learn without overfitting the training data. Finally, the low-count network input was multiplied by the dose reduction factor in order to accelerate network training and remove the need to learn to scale the output by this factor. Both models were trained on a computer with an Intel® Core™ (trademarks of Intel Corporation) i9-7980XE 18-core processor, 128 GB memory, and two GeForce® (a registered trademark of NVIDIA Corporation) GTX 1080 Ti graphics cards running Ubuntu 18.04 (Bionic Beaver), Python 2.7.15 (Python Software Foundation), TensorFlow 1.14.0.

PET data for this illustrative comparison was extracted from an Institutional Review Board (IRB) approved psychiatric study. A total of 35 subjects (approximately 3500 slabs) were acquired. Each subject was administered between 148-185 MBq (4-5 mCi) of $^{18}$F-FDG and asked to void their bladder immediately after injection. This ongoing study acquired listmode data using a dedicated MRI head coil for 60 minutes immediately following bladder clearing using a Siemens Biograph mMR PET/MRI scanner. Attenuation maps were generated using an established MRI-based algorithm, such as, for example, the "Boston Method." (See, e.g., K. T. Chen, et al., "On the Accuracy and Reproducibility of a Novel Probabilistic Atlas-Based Generation for Calculation of Head Attenuation Maps on Integrated PET/MR Scanners," *European Journal of Nuclear Medicine and Molecular Imaging*, 2017, 44(3), pp. 398-407; and C. B. Poynton, et al., "Probabilistic Atlas-Based Segmentation of Combined T1-Weighted and DUTE MRI for Calculation of Head Attenuation Maps in Integrated PET/MRI Scanners," *American Journal of Nuclear Medicine and Molecular Imaging*, 2014, 4(2), p. 160, the disclosures of which are incorporated by reference herein in their entireties). Scanner attenuation maps were also extracted for reconstruction.

Data were prepared using a Siemens e7-tools package. Low-count PET data were generated through Poisson thinning. Table 1 below shows count statistics measuring mean counts and standard deviation across all subjects for full-count (ground truth) and low-count (Poisson thinned) from listmode data; low-count data consists of about 10% of ground truth counts.

TABLE 1

| | Mean Counts ± Standard Deviation ($\times 10^9$) |
|---|---|
| Full-count | 1.5733 ± 0.3786 |
| Low-count | 0.1497 ± 0.0360 |

Table 2 below displays mean total activity and standard deviation, in arbitrary units (a.u.), in the entire FOV across all subjects for all image types. Specifically, low-count PET data with a dose reduction factor of 90% (i.e., one-tenth of original counts) were generated. PET images were reconstructed using Siemens e7-tools with ordered subset expectation maximization (OSEM: 6 iterations, 21 subsets).

TABLE 2

| | Mean Activity ± Standard Deviation ($\times 10^{10}$) |
|---|---|
| Full-count | 2.6933 ± 0.5088 |
| dNet | 2.5885 ± 0.5005 |
| U-Net | 2.5883 ± 0.5035 |
| Gaussian** | 2.6001 ± 0.4891 |
| Low-count | 0.2600 ± 0.0489 |

(**Gaussian filtered images were corrected for activity by multiplying dose reduction factor (10×))

Figure 4:
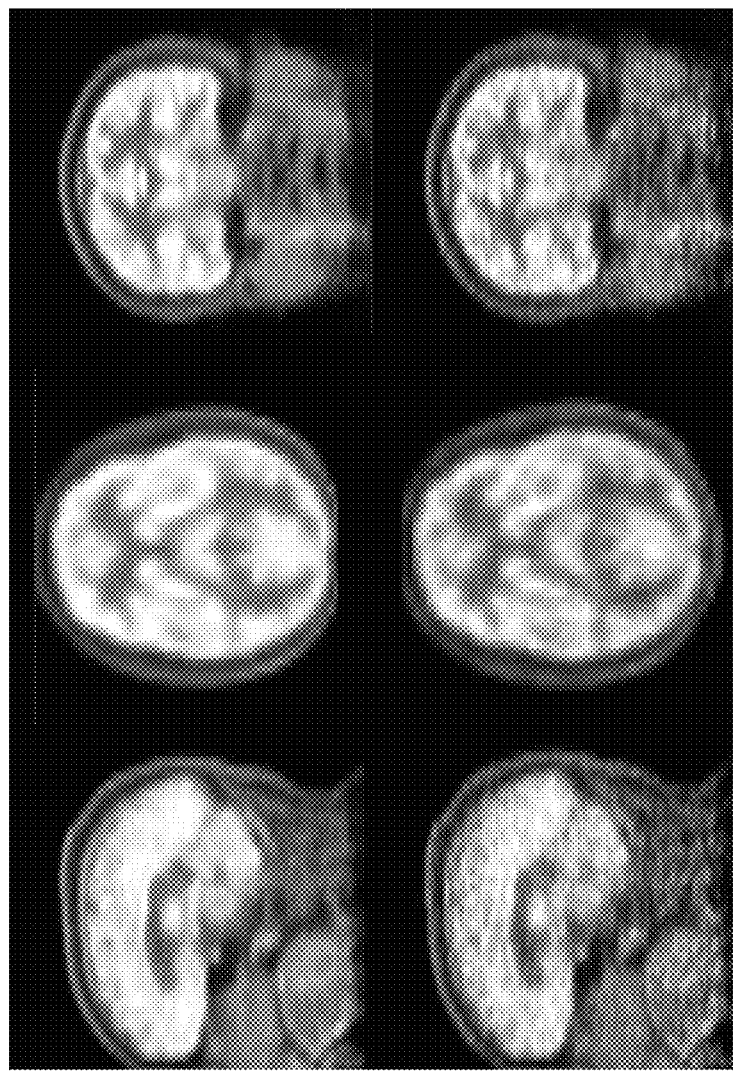
FIG. 4 shows sagittal, transverse and coronal views corresponding to full-count data and low-count data (60-minute listmode) after being reconstructed using ordered subset expectation maximization (OSEM)

Static images were reconstructed using emission data acquired between 50 and 60 minutes after injection. FIG. 4 shows sagittal, transverse and coronal views corresponding to full-count data and low-count data (60-minute listmode) after being reconstructed using ordered subset expectation maximization (OSEM). As apparent from FIG. 4, the low-count PET image appears grainy and noisy.

A primary objective metric of the image quality in this exemplary study is the mean absolute percent error (MAPE) of the denoising methods (e.g., CNN-denoised data) relative to the full-count dataset. MAPE can be defined as:

$$MAPE(x, y) = \frac{1}{n}\sum_{i=1}^{n}\left|\frac{y_i - x_i}{y_i}\right|, \quad (1)$$

where $y_i$ is the $i^{th}$ voxel in the ground truth image (y) and $x_i$ is the $i^{th}$ voxel in the denoised PET data.

Other quantitative image quality metrics widely accepted in the field were also studied, including peak signal-to-noise ratio (PSNR) and structural similarity index (SSIM) for the full-count reconstructed PET data and resultant denoised images. PSNR is an objective measure of image quality defined as:

$$PSNR(x, y) = 20 \cdot \log_{10}\left(\frac{MAX(y)}{\sqrt{MSE(x, y)}}\right), \quad (2)$$

where y is the signal of the ground truth full-count PET data, x is the signal from the denoised PET data, MAX indicates maximum signal and MSE indicates the mean squared error between the two signal intensities. SSIM is more complex and accounts for patch-wise image statistics and is defined as:

$$SSIM(x, y) = \frac{(2\mu_x\mu_y + c_1)(2\sigma_{xy} + c_2)}{(\mu_x^2 + \mu_y^2 + c_1)(\sigma_x^2 + \sigma_y^2 + c_2)}, \quad (3)$$

where y is the signal of the patch-wise ground truth full-count PET data, x is the signal of the patch-wise denoised PET data, $\sigma_x$ represents the variance of x, $\sigma_y$ represents the variance of y, $\sigma_{xy}$ represents the covariance of x and y, $\mu_x$ represents the mean of x, $\mu_y$ represents the mean of y, and $c_1$ and $c_2$ are stabilizing terms.

Given that this dataset consists of a psychiatric cohort of patients with depression, quantitative analysis was conducted on ROIs relevant to the disease. ROIs used for this analysis include the hippocampus, amygdala, temporal and frontal lobes, as they have been shown to be associated with depression. MAPE, relative to full-count image, was the figure of merit utilized to determine the quantitative results across dNet and U-Net and Gaussian filtering.

Figure 5:
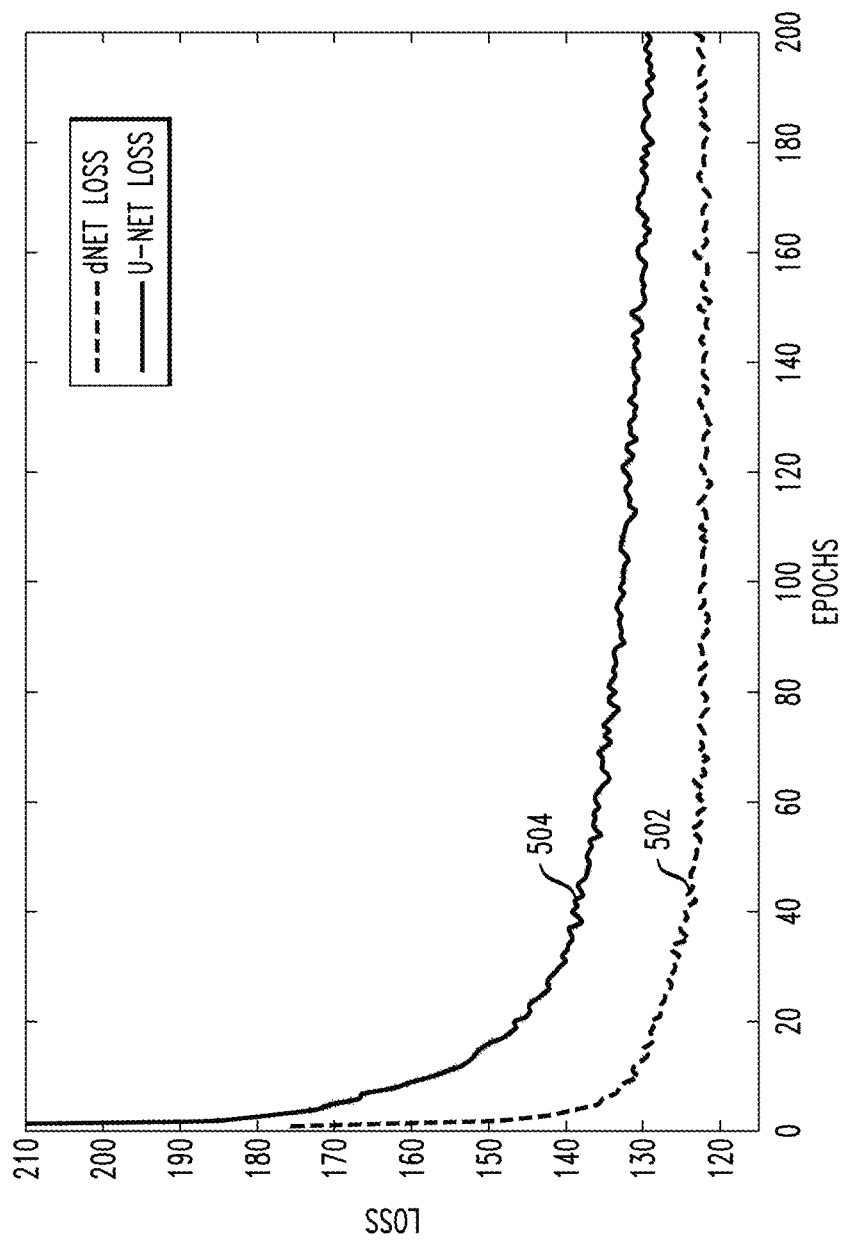
FIG. 5 is a graph depicting a convergence curve of the loss function for dNet and U-Net averaged over all leave-one out cross validation models.

Both the dNet, according to embodiments of the invention, and U-Net were successfully trained to synthesize full-count PET images from low-count PET images after 200 epochs. FIG. 5 is a graph depicting a convergence curve of the loss function for dNet and U-Net averaged over all leave-one out cross validation models. The graph shown in FIG. 5 indicates that the models have converged over the course of 200 epochs, and that the loss attributable to dNet, as represented by plot 502, is significantly reduced compared to the loss attributable to U-Net, as represented by plot 504.

Figure 6A:
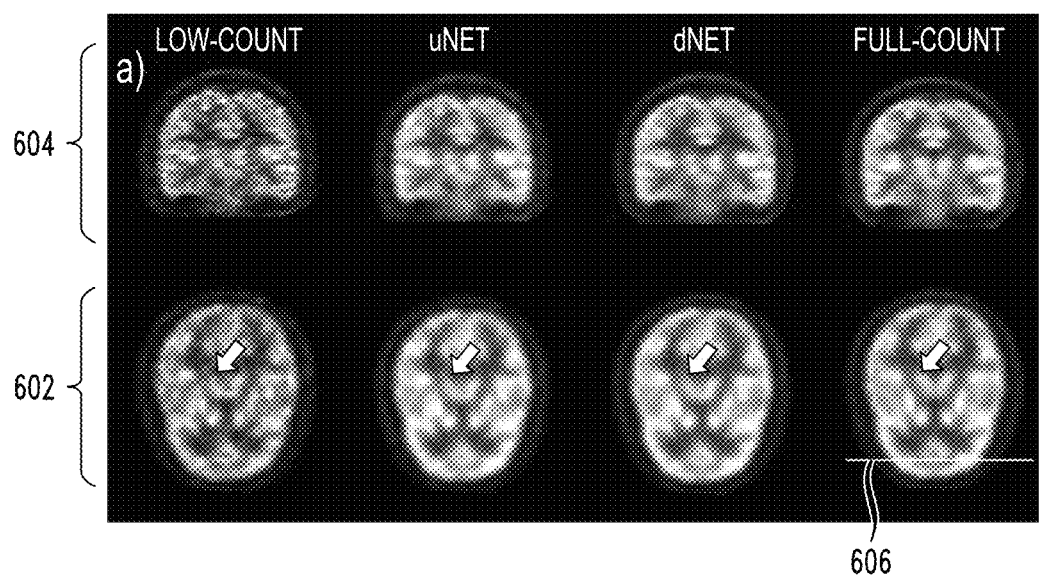
FIG. 6A depicts illustrative sets of reconstructed low-count, U-Net, dNet and full-count images corresponding to coronal and transverse slices, according to an embodiment of the invention.
Figure 6B:
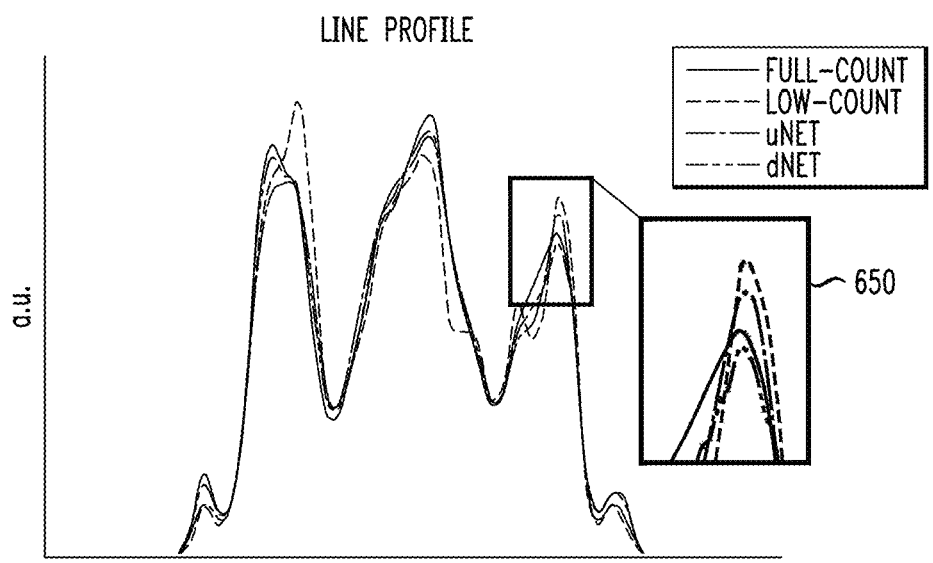
FIG. 6B is a graph depicting a line profile that represents arbitrary units (a.u.) of activity corresponding to an indicated line in FIG. 6A, according to an embodiment of the invention.

For a randomly chosen subject, FIG. 6A depicts illustrative sets, 602 and 604, of reconstructed low-count, U-Net, dNet and full-count (reconstructed from full count 10-min emission data) images corresponding to coronal and transverse slices, respectively, according to an embodiment of the invention. FIG. 6B is a graph depicting a line profile that represents arbitrary units (a.u.) of activity corresponding to a line 606 in FIG. 6A, according to an embodiment of the invention. Upon subjective visual inspection, both U-Net and dNet were able to show improvement compared to the low-count image. As apparent from FIG. 6A, both CNN models yielded images similar to the images reconstructed with full-count data by removing the noise in the low-count images. The arrow in each of the images points to a region where an edge was difficult to differentiate in the low-count images, but recovered in both CNN denoised images.

To better visualize the improvement afforded by dNet, line profiles of the line 606 shown in the FIG. 6A are illustrated in FIG. 6B. As shown in box 650, dNet yields line profiles that more closely track the full-count curve compared to U-Net; that is, dNet yields a smaller absolute difference from the full-count image relative to U-Net.

Figure 7:
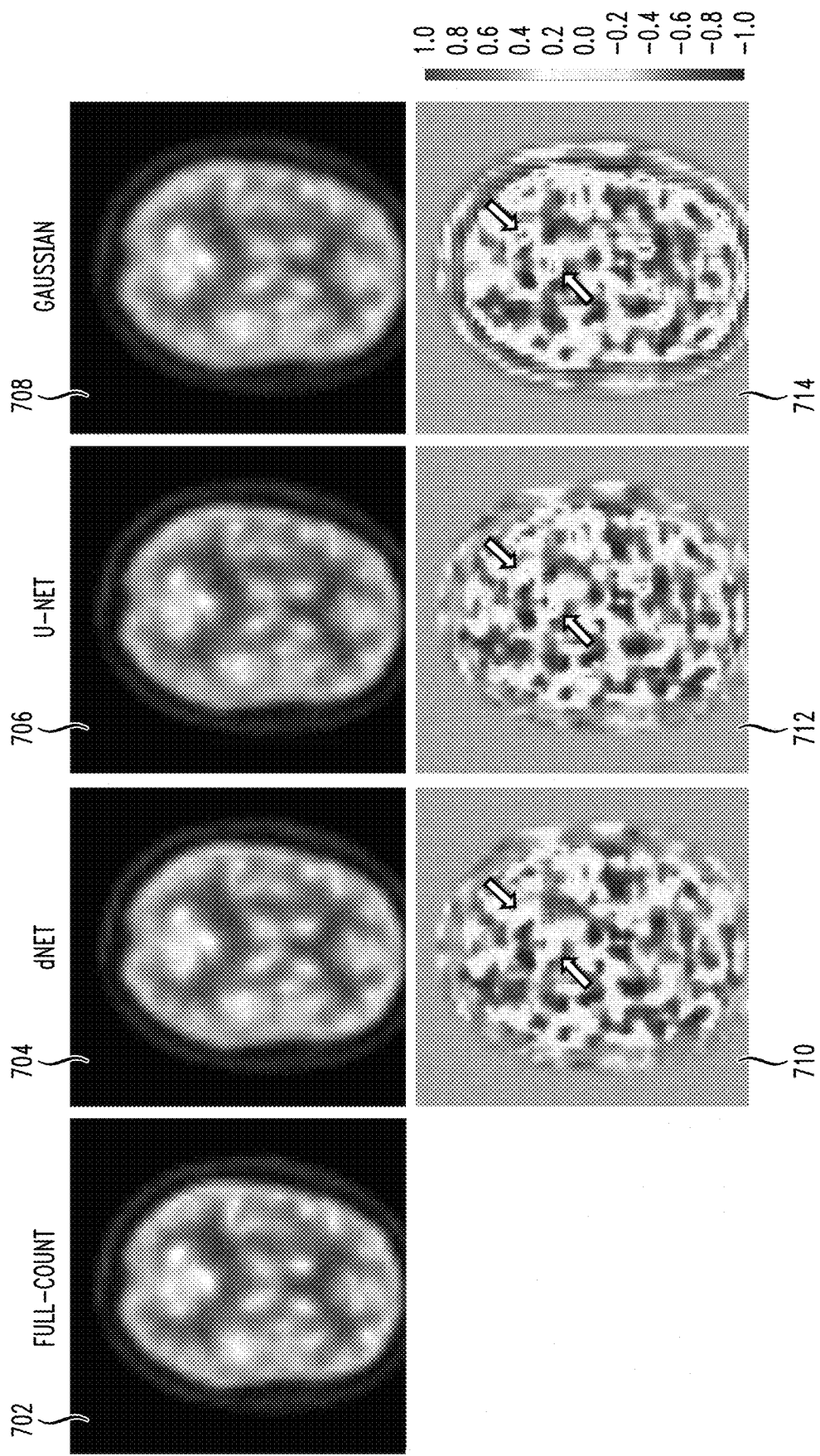
FIG. 7 depicts full-count, dNet, U-Net, and Gaussian filtered PET images along with difference maps corresponding to the dNet, U-Net and Gaussian filtered PET images, according to an embodiment of the invention.

Likewise, FIG. 7 depicts full-count 702, dNet 704, U-Net 706, and Gaussian filtered 708 PET images along with difference maps 710, 712 and 714 corresponding to the dNet, U-Net and Gaussian filtered PET images, respectively, according to an embodiment of the invention. Highlighted by arrows are areas of the respective images 710-714 in which dNet recovers counts better than U-Net and Gaussian filtering.

Mean and standard deviation of the objective imaging metrics are shown in Table 3 below. The data presented in Table 3 is shown graphically in FIG. 8.

TABLE 3

| Model | Structural Similarity Index (SSIM) | Peak Signal-to-Noise Ratio (PSNR) | Mean Absolute Percent Error (MAPE) |
|---|---|---|---|
| Low-count | 0.9190 ± 0.0243 | 28.42 ± 1.59 dB | 7.48 ± 1.39 |
| U-Net | 0.9447 ± 0.0178 | 31.05 ± 1.39 dB | 5.31 ± 0.76 |
| dNet | 0.9513 ± 0.0154** | 31.55 ± 1.31 dB** | 4.99 ± 0.68** |
| Gaussian | 0.9271 ± 0.0148 | 29.26 ± 1.11 dB | 6.53 ± 0.62 |

(Statistically significant differences found between dNet and U-Net using a paired t-test:**p<0.01)

The first row represents objective measures of the low-count PET image as compared to the ground truth, full-count PET image. Rows 2 and 3 show metrics calculated after the denoising of all subjects using the two different CNN models. An objective improvement in image quality is reflected by larger values in PSNR or SSIM and smaller values in MAPE. Exemplary results demonstrate that U-Net and dNet were both effective at denoising the low-count image. When considering full-count image as our ground truth for all image metrics, MAPE was improved from low-count images when denoising with U-Net, dNet and Gaussian filtering (7.48±1.39 vs. 5.31±0.76, 4.99±0.68, 6.53±0.62, respectively). PSNR was also improved from low-count images when denoising with U-Net (28.42±1.59 dB vs. 31.05±1.39 dB, $p<0.01$), dNet (28.42±1.59 dB vs. 31.55±1.31 dB, $p<0.001$) and Gaussian filter (28.42±1.59 dB vs. 29.26±1.11 dB, $p<0.05$). SSIM was also shown to be significantly improved from low-count images to U-Net (0.9190±0.0243 vs. 0.9447±0.0178, $p<0.05$), dNet (0.9190±0.0243 vs. 0.9513±0.0154, $p<0.01$) and Gaussian filtering (0.9190±0.0243 vs. 0.9271±0.0148, $p<0.05$). Using a paired samples t-test, the dNet model according to aspects of the invention significantly outperformed U-Net across all metrics ($p<0.01$).

Figure 8:
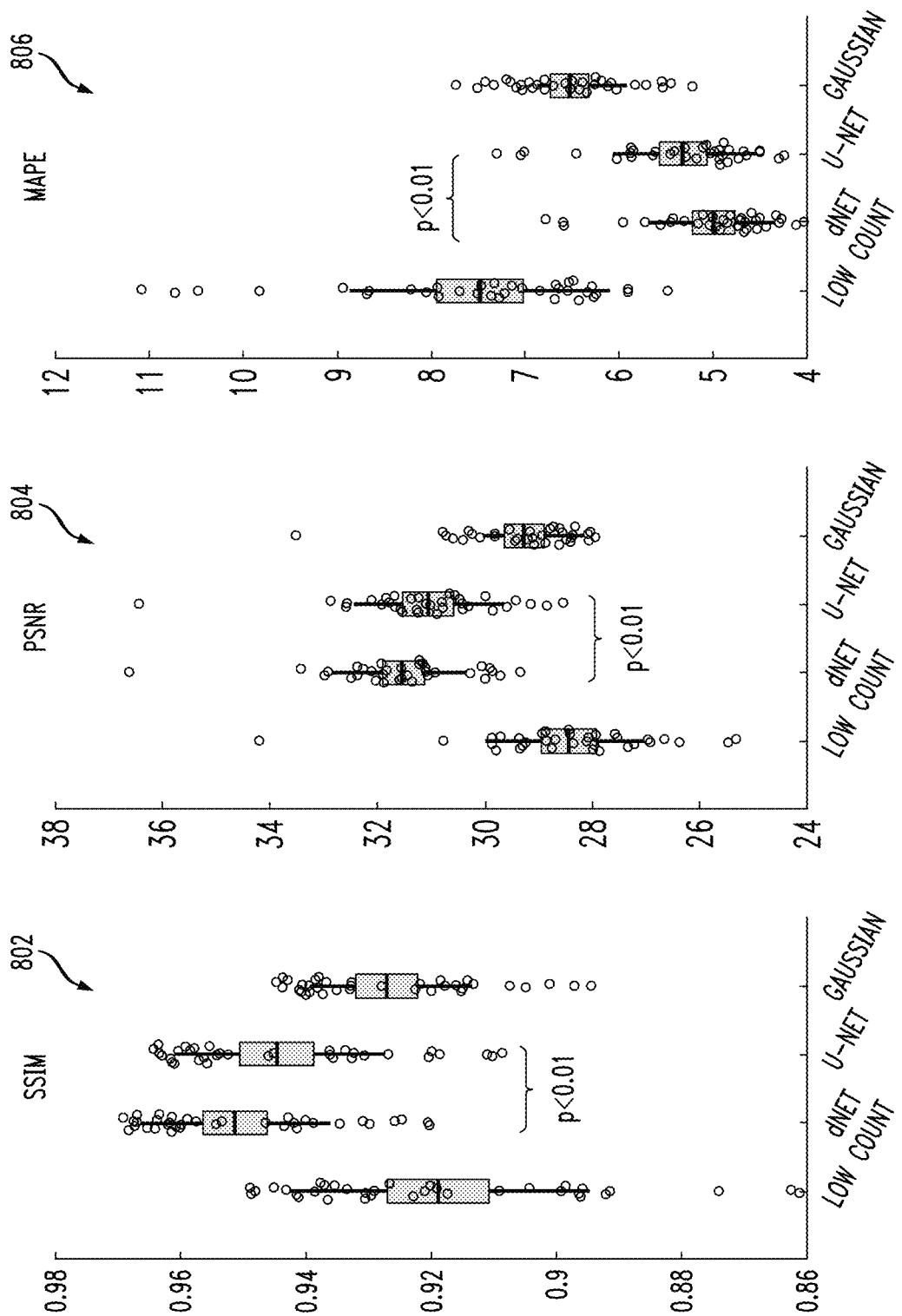
FIG. 8 are graphs depicting plotted image quality metrics for the illustrative reconstructed low-count, dNet, U-Net and Gaussian PET images shown in FIG. 7 using a leave-one out cross-validation approach, according to an embodiment of the invention.

FIG. 8 are graphs conceptually depicting plotted image quality metrics for the illustrative reconstructed low-count, dNet, U-Net and Gaussian PET images shown in FIG. 7 using a leave-one out cross-validation approach, according to an embodiment of the invention. The image quality metrics used in FIG. 8 include SSIM 802, PSNR 804, and MAPE 806, although it is to be appreciated that other metrics for comparing image quality are similarly contemplated by the invention. In each metric shown in FIG. 8, each shaded box indicates a 95% confidence interval (CI), the vertical line represents one standard deviation, the horizontal line represents mean, and circles indicate measured data for each subject. As apparent from FIG. 8, within each objective metric, all three denoising methods improve upon the low-count images; wherein both CNN models outperformed the Gaussian filtering method. dNet also significantly outperformed U-Net across all metrics ($p<0.01$). Specifically, each subject had higher PSNR and SSIM values and lower MAPE values using dNet compared to U-Net.

Figure 9:
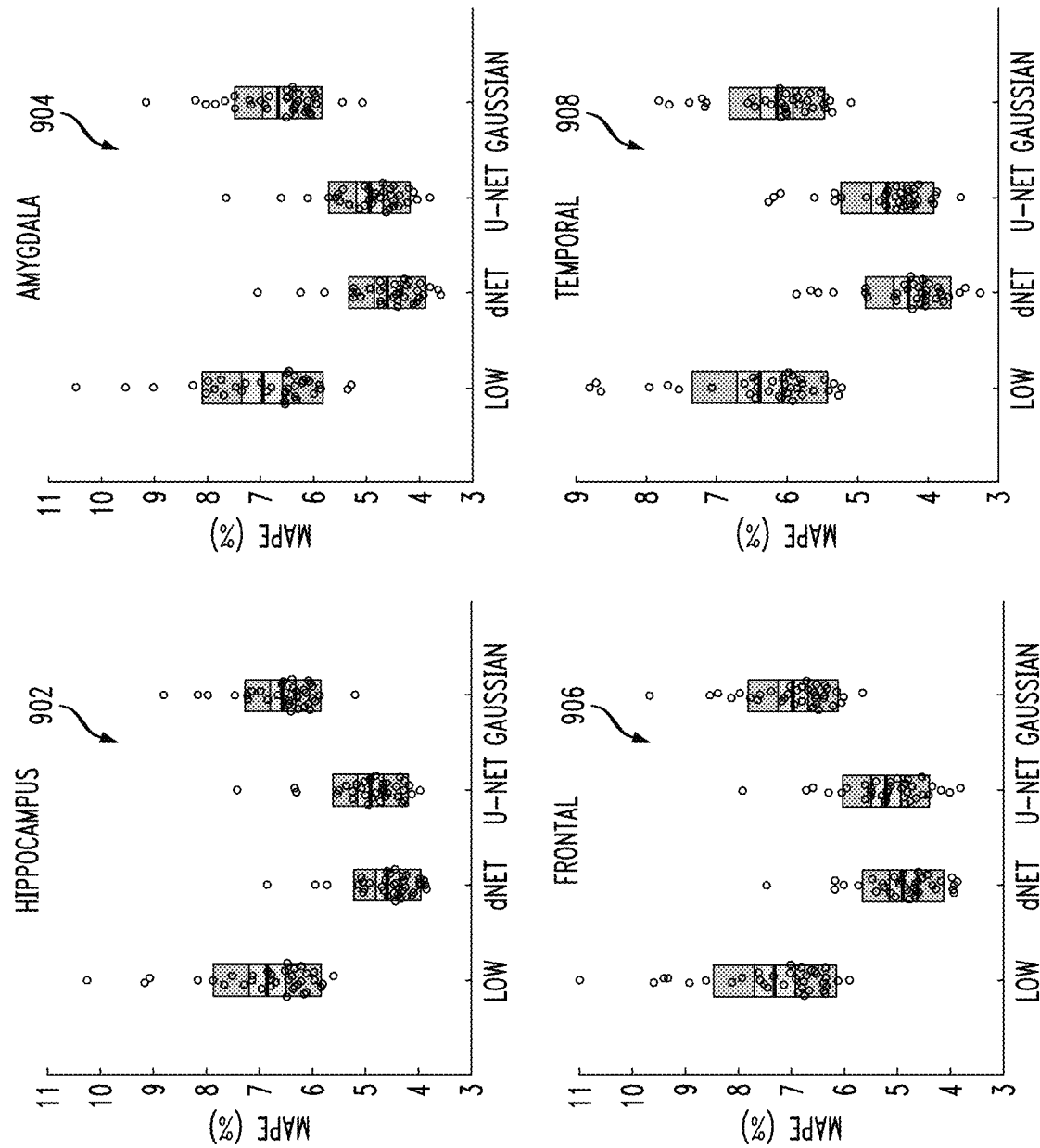
FIG. 9 shows exemplary plots of mean absolute percent error (MAPE) relative to full-count images for reconstructed dNet, U-Net, low-count and Gaussian filtered images for the hippocampus, amygdala, frontal and temporal lobes, according to an embodiment of the invention.

Further quantitative analysis shows that both CNNs demonstrated superior performance in ROI quantification compared to Gaussian filtering. For example, ROI analysis across four ROI's relevant to depression showed that dNet had lower MAPE compared to U-Net, Gaussian filtering and low-count images. FIG. 9 shows exemplary plots of MAPE relative to full-count images for reconstructed dNet, U-Net, low-count and Gaussian filtered images for the hippocampus 902, amygdala 904, frontal lobe 906, and temporal lobe 908, according to an embodiment of the invention. For each ROI shown in FIG. 9, each light shaded box indicates the 95% CI, the dark shaded box represents one standard deviation, the horizontal line represents the mean, and circles represent measured data for each subject. Across these illustrative ROIs, dNet outperformed all other denoising schemes in ROI quantification.

Figure 10:
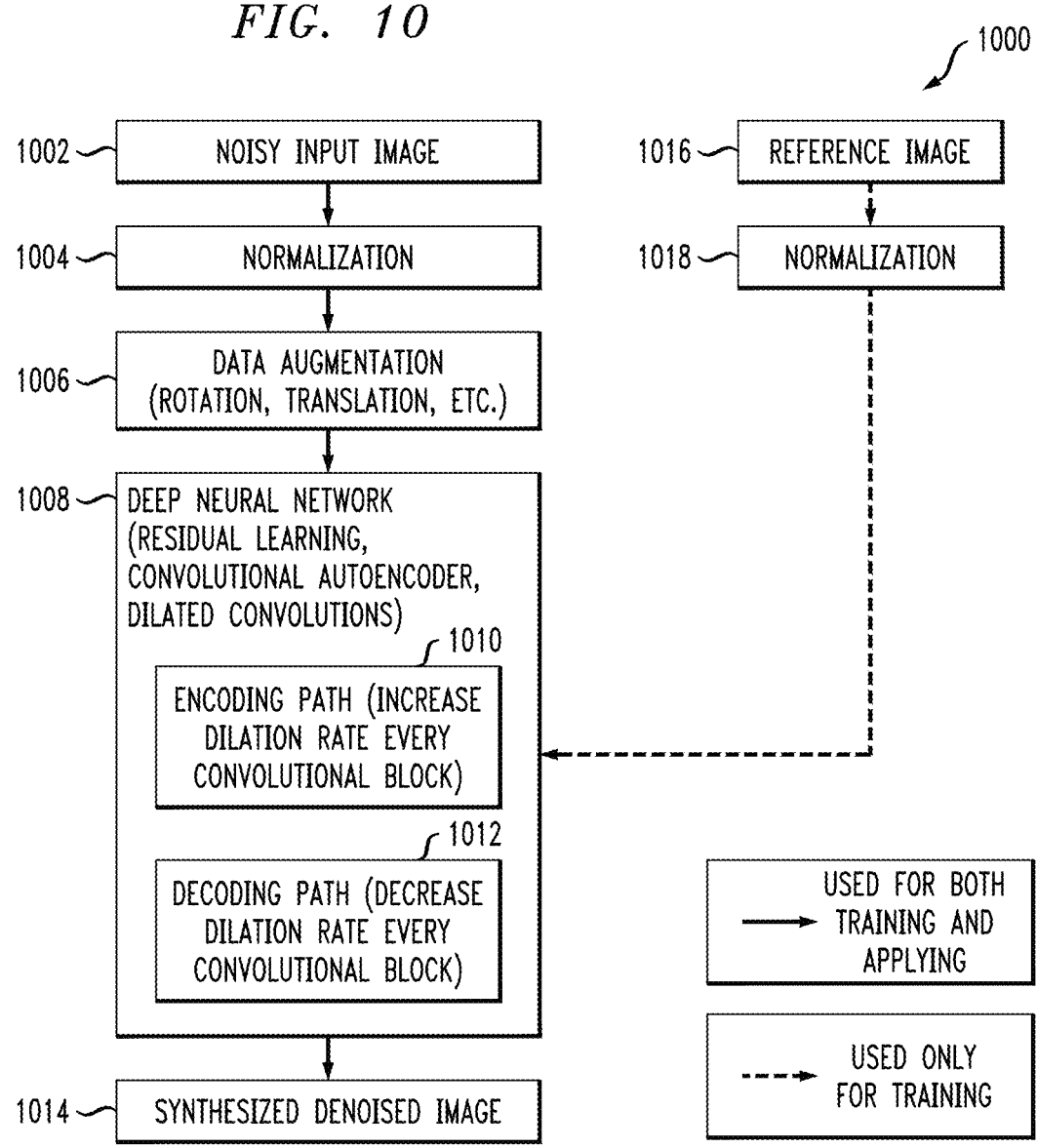
FIG. 10 is a flow diagram depicting at least a portion of an exemplary method 1000 for PET image denoising, according to an embodiment of the present invention.

FIG. 10 is a flow diagram depicting at least a portion of an exemplary method 1000 for PET image denoising, according to an embodiment of the invention. With reference to FIG. 10, the method 1000 begins, by obtaining one or more noisy input images in step 1002. Such noisy input images may be low-count PET images that require image enhancement to improve the quality thereof. In step 1004, the noisy input image is normalized. In image processing, normalization often involves changing the range of pixel intensity values, to thereby optimize image contrast. Normalization is sometimes called contrast stretching or histogram stretching, which is employed to expand the dynamic range of the image.

The normalized image data generated in step 1004 is then augmented in step 1006, which may include, for example, image rotation, translation, etc. The augmented image data generated in step 1006 is then supplied to a deep neural network in step 1008 which is configured to perform residual learning, convolutional encoding and dilated convolutions, among other image processing. In one or more embodiments, the deep neural network includes an encoding path 1010, configured to increase dilation rate every convolutional block, and a decoding path 1012, configured to decrease dilation rate every convolutional block.

The output data generated by the deep neural network in step 1008 is added to the input of 1008 to create the synthesized uncorrupted image in step 1014; this is the final step of the apparatus 1000. In one or more embodiments, step 1014 is implemented by simply adding the input image to the residual image, for example using an adder 156 as shown in FIG. 1B.

For purposes of training the deep neural network in step 1008, a reference image may be obtained in step 1016. In one or more embodiments, this reference image is generated from reconstructing the untouched listmode data, as previously mentioned, to create PET images consistent with full-count images as shown in FIG. 4. The reference image is normalized in step 1018. Image normalization in step 1018 may be performed using a scheme consistent with the approach used in step 1004. Alternatively, a different image normalization scheme can be employed. The normalized reference image data generated in step 1018 is then provided to the deep neural network in step 1008 and is used to train the network.

Figure 11:
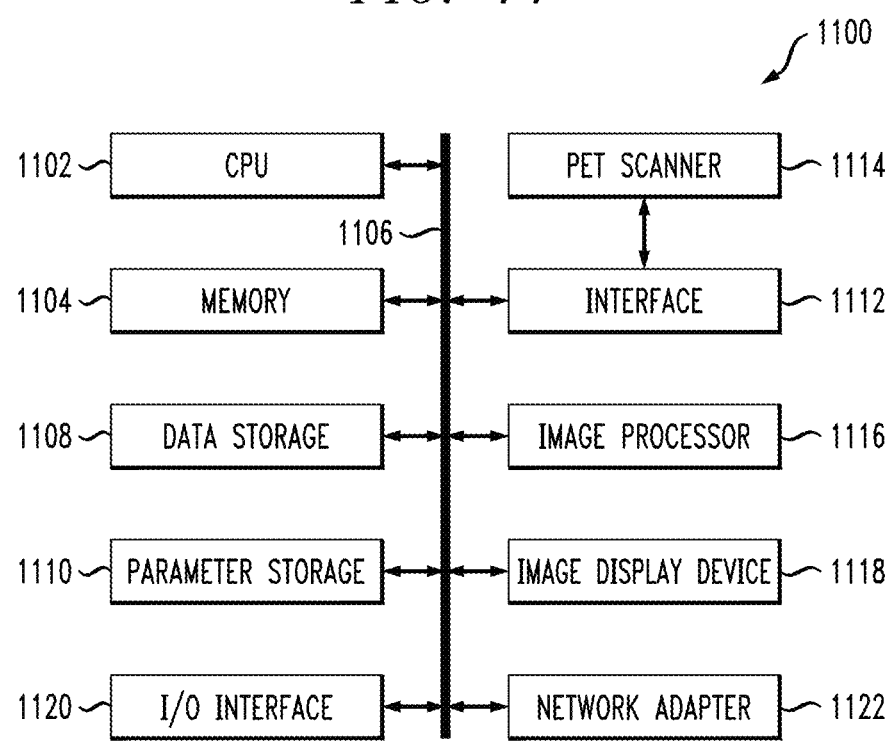
FIG. 11 is a block diagram depicting at least a portion of an exemplary apparatus for implementing a low-count PET image denoising pipeline configured to decrease subject burden without sacrificing image quality, according an embodiment of the present invention.

Embodiments of the invention may be implemented together with virtually any type of computer or processor, regardless of the platform being suitable for storing and/or executing program code. By way of example only and without limitation, FIG. 11 is a block diagram depicting at least a portion of an exemplary computing system 1100 suitable for executing program code for implementing a low-count PET image denoising pipeline, according an embodiment of the invention. The computing system 1100 is only one example of a suitable computer system and is not intended to suggest any limitation as to the scope of use or functionality of embodiments of the invention described herein, regardless, whether the computer system 1100 is capable of being implemented and/or performing any of the functionality set forth hereinabove.

In the computing system 1100, there are components that are adapted for connection to and operational with numerous other general-purpose and/or special-purpose computing system environments or configurations. Examples of well-known computing systems, environments, and/or configurations that may be suitable for use with the computing system 1100 include, but are not limited to, personal computer systems, server computer systems (i.e., servers), thin clients, thick clients, hand-held or laptop devices, mobile devices, multiprocessor systems, microprocessor-based systems, programmable consumer electronics, network PCs, minicomputer systems, mainframe computer systems, and distributed cloud computing environments that include any of the above systems or devices, and the like.

The computing system 1100 may be described in the general context of computer system-executable instructions, such as program modules, being executed by the computing system 1100. Generally, program modules may include routines, programs, objects, components, logic, data structures, and so on that perform particular tasks or implement particular abstract data types. The computing system 1100 may be practiced in distributed cloud computing environments where tasks are performed by remote processing devices that are linked through a communications network.

In a distributed cloud computing environment, program modules may be located in both local and remote computer system storage media, including memory storage devices.

As shown in FIG. 11, components of computing system 1100 may include, but are not limited to, at least one processors or central processing unit (CPU) 1102, a system memory 1104, and a bus 1106 that couples various system components including the system memory 1104 to the CPU 1102. Bus 1106 represents one or more of any of several types of bus structures, including a memory bus or memory controller, a peripheral bus, an accelerated graphics port, and a processor or local bus using any of a variety of bus architectures. By way of example, and without limitation, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 1100 typically includes a variety of computer system readable media. Such media may be any available media that is accessible by computing system 1100, and it includes both, volatile and non-volatile media, removable and non-removable media.

The system memory 1104 may be used for at least temporarily storing intermediate computation results of the CPU 1102 and/or data provided to the CPU as inputs thereto. The system memory 1104 preferably includes computer system readable media in the form of volatile memory, such as random-access memory (RAM) and/or cache memory. The computing system 1100 may further include other removable/non-removable, volatile/non-volatile computer readable storage media. By way of example only, a data storage unit 1108 may be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media may be provided. In such instances, each can be connected to the bus 1106 by one or more data media interfaces. As will be further depicted and described below, memory 1104 may include at least one program product having a set (e.g., at least one) of program modules that are configured to carry out the functions of embodiments of the invention.

The computing system 110 may also include a parameter storage unit 1110. The parameter storage unit 1110 is coupled to the bus 1106 and is adapted to convey parameter data to one or more other computing system components, including the CPU 1102. In one or more embodiments, at least a portion of the data storage unit 1108 and/or parameter storage unit 1110 may be incorporated into the system memory 1104. For example, the system memory 1104 may be partitioned into separate storage areas for storing data and parameters otherwise allocated to separate data storage or parameter storage units 1108 or 1110, respectively.

An interface device 1112 included in the computing system 1100 is preferably coupled to the bus 1106 and is configured to handle communications between a PET scanner 1114 and other components in the computing system 1100, such as the CPU 1102. The PET scanner 1114 provides to the computing system 1100 input image data (e.g., low-count PET image data) which is to be processed to enhance the quality thereof. The computing system 1100 includes, in one or more embodiments, a dedicated image processor 1116 configured to perform at least a portion of the image processing steps according to aspects of the invention, for example as described in conjunction with FIG. 10. Results of the image processing performed by the computing system 1100, which may include reconstructed denoised PET images, are displayed on an image display device 1118 for viewing by a user. As previously stated, the denoised PET images provide the user with enhanced image quality to thereby facilitate a more accurate medical diagnosis, among other advantages.

A program/utility, having a set (at least one) of program modules, may be stored in memory 1104 by way of example, and not limiting, as well as an operating system, one or more application programs, other program modules, and program data. Each of the operating systems, one or more application programs, other program modules, and program data or some combination thereof, may include an instantiation of a networking environment. The program modules generally carry out the functions and/or methodologies of embodiments of the invention, as described herein.

The computing system 1100 may also communicate with one or more external devices, including, for example, a keyboard, a pointing device, a display, etc.; one or more devices that enable a user to interact with the computing system 1100; and/or any devices (e.g., network card, modem, etc.) that enable the computing system 1100 to communicate with one or more other computing devices. Such communication can occur via one or more input/output (I/O) interfaces 1120. Still yet, the computing system 1100 may communicate with one or more networks such as a local area network (LAN), a general wide area network (WAN), and/or a public network (e.g., the Internet) via a network adapter 1122. As depicted, the network adapter 1122 may communicate with the other components of the computing system 1100 via the bus 1106. Although not explicitly shown, other hardware and/or software components could be used in conjunction with the computing system 1100. Examples, include, but are not limited to: microcode, device drivers, redundant processing units, external disk drive arrays, redundant array of independent disks (RAID) systems, tape drives, and data archival storage systems, etc.

Additionally, further components of the system for PET image denoising may be connected to the bus 1106. This may include, for example, one or more image preprocessing modules configured to perform image preprocessing (e.g., image normalization 1004, 1018 in FIG. 10), a data augmentation module configured to perform image rotation, translation, etc. (e.g., 1006 in FIG. 10), a deep neural network configured to perform image encoding and decoding (e.g., convolutions, etc. in 1010, 1012 of FIG. 10), and a synthesis module for constructing the denoised output image(s) (e.g., 1014 in FIG. 10).

The present invention may be a system, a method, and/or a computer program product at any possible technical level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not intended to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire or the air.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission routers, firewalls, switches, gateway computers and/or edge servers. A network adapter card or network interface in each computer/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer, for example, through the Internet using an Internet Service Provider (ISP). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize and configure the electronic circuitry, in order to perform aspects of the present invention.

Aspects of the present invention are described herein with reference to flowchart instructions and/or block diagrams of methods, apparatus (systems), and computer program products according to embodiments of the invention. It will be understood that each block of the flowchart instructions and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram blocks or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be appreciated that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The illustrations of embodiments described herein are intended to provide a general understanding of the various embodiments, and they are not intended to serve as a complete description of all the elements and/or features of apparatus, methods and systems that might make use of the techniques described herein. Many other embodiments will become apparent to those skilled in the art given the teachings herein; other embodiments are utilized and derived therefrom, such that structural and logical substitutions and changes can be made without departing from the scope of this disclosure. It should also be noted that, in some alternative implementations, some of the steps of exemplary methods described herein may occur out of the order described or noted in the figures (where shown). The drawings are also merely representational and are not drawn to scale. Accordingly, the specification and drawings are to be regarded in an illustrative rather than a restrictive sense.

Reference made throughout this specification to "one embodiment" or "an embodiment" is intended to mean that a particular feature, structure, or characteristic described in connection with the embodiment is included in at least one embodiment of the claimed subject matter. It is to be understood that appearances of the phrase "in one embodiment" or "an embodiment" are not necessarily all referring to the same embodiment. Furthermore, embodiments may be referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it is to be appreciated that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below," where used, are intended to indicate positioning of elements or structures relative to each other as opposed to absolute elevation.

The corresponding structures, materials, acts, and equivalents of any means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit thereof. The embodiments were chosen and described in order to best explain principles and practical applications, and to enable others of ordinary skill in the art to understand the various embodiments with various modifications as are suited to the particular use contemplated.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, the claimed subject matter may lie in less than all features of a single embodiment. Thus, the following claims are hereby incorporated into the Detailed Description, with each claim standing on its own as separately claimed subject matter.

Given the teachings provided herein, one of ordinary skill in the art will be able to contemplate other implementations and applications of the techniques and disclosed embodiments according to aspects of the invention. Although illustrative embodiments have been described herein with reference to the accompanying drawings, it is to be understood that illustrative embodiments are not limited to those precise embodiments, and that various other changes and modifications may be made therein by one skilled in the art without departing from the scope or spirit of the appended claims.

What is claimed is:

1. A method for performing positron emission tomography (PET) image denoising using a dilated convolutional neural network system, the method comprising:
    obtaining, as an input to the dilated convolutional neural network system, a noisy image;
    performing image normalization on the noisy image to generate normalized image data corresponding to the noisy image;
    encoding the normalized image data using one or more convolutions in the dilated convolutional neural network, whereby a dilation rate is increased for each encoding convolution performed to generate encoded image data;
    decoding the encoded image data using one or more convolutions in the dilated convolutional neural network, whereby dilation rate is decreased for each decoding convolution performed to generate decoded image data;
    synthesizing the decoded image data to construct a denoised output image corresponding to the noisy image; and
    displaying the denoised output image on an image display device, the denoised output image having enhanced image quality compared to the noisy image.

2. The method of claim 1, further comprising:
    obtaining a reference image representing a full-count image of the noisy image;
    performing image normalization on the reference image to generate normalized reference image data corresponding to the reference image; and
    training the dilated convolutional neural network using the normalized reference image data.

3. The method of claim 2, wherein training the dilated convolutional neural network comprises utilizing the normalized reference image data in at least a part of the encoding of the normalized image data and/or the decoding of the encoded image data.

4. The method of claim 2, wherein obtaining the reference image comprises generating the reference image by reconstructing untouched listmode data to create PET images consistent with full-count images corresponding to the noisy image.

5. The method of claim 1, wherein the dilation rate is increased or decreased by a prescribed factor for each subsequent encoding convolution or decoding convolution, respectively.

6. The method of claim 5, wherein the prescribed factor is equal to two.

7. The method of claim 1, wherein the denoised output image comprises uncorrupted PET data generated by summing corrupted PET image data corresponding to the noisy image with residual image data, the residual image data comprising a prescribed mapping from corrupted to uncorrupted PET data without a need for data fitting.

8. The method of claim 1, further comprising augmenting the normalized image data to generate augmented image data, the augmented image data being used for encoding the normalized image data.

9. The method of claim 8, wherein augmenting comprising at least one of image translation and image rotation.

10. An apparatus for performing positron emission tomography (PET) image denoising, the apparatus comprising:
  memory; and
  at least one processor coupled to the memory, the at least one processor implementing a dilated convolutional neural network and being configured:
    to obtain, as an input to the dilated convolutional neural network, a noisy image;
    to perform image normalization on the noisy image to generate normalized image data corresponding to the noisy image;
    to encode the normalized image data using one or more convolutions in the dilated convolutional neural network, whereby a dilation rate is increased for each encoding convolution performed to generate encoded image data;
    to decode the encoded image data using one or more convolutions in the dilated convolutional neural network, whereby dilation rate is decreased for each decoding convolution performed to generate decoded image data;
    to synthesize the decoded image data to construct a denoised output image corresponding to the noisy image; and
    to display the denoised output image on an image display device, the denoised output image having enhanced image quality compared to the noisy image.

11. The apparatus of claim 10, wherein the at least one processor is further configured:
  to obtain a reference image representing a full-count image of the noisy image;
  to perform image normalization on the reference image to generate normalized reference image data corresponding to the reference image; and
  to train the dilated convolutional neural network using the normalized reference image data.

12. The apparatus of claim 11, wherein the at least one processor is further configured to train the dilated convolutional neural network by utilizing the normalized reference image data in at least a part of encoding the normalized image data and/or decoding the encoded image data.

13. The apparatus of claim 11, wherein the at least one processor is further configured to generate the reference image by reconstructing untouched listmode data to create PET images consistent with full-count images corresponding to the noisy image.

14. The apparatus of claim 10, wherein the at least one processor is configured to increase the dilation rate or to decrease the dilation rate by a prescribed factor for each subsequent encoding convolution or decoding convolution, respectively.

15. The apparatus of claim 14, wherein the prescribed factor is equal to two.

16. The apparatus of claim 10, further comprising an adder, the adder being configured to generate the denoised output image comprising uncorrupted PET data by summing corrupted PET image data corresponding to the noisy image with residual image data, the residual image data comprising a prescribed mapping from corrupted to uncorrupted PET data without a need of a direct fit.

17. The apparatus of claim 10, wherein the at least one processor is further configured to augment the normalized image data to generate augmented image data, the augmented image data being used to encode the normalized image data.

18. The apparatus of claim 17, wherein the at least one processor is further configured to augment the normalized image data by performing at least one of image translation and image rotation.

19. A computer program product, the computer program product comprising a non-transitory computer readable storage medium having computer readable program code embodied thereon for performing positron emission tomography (PET) image denoising, the computer readable program code, when executed on at least one processor, causing the at least one processor:
  to obtain, as an input to the dilated convolutional neural network, a noisy image;
  to perform image normalization on the noisy image to generate normalized image data corresponding to the noisy image;
  to encode the normalized image data using one or more convolutions in the dilated convolutional neural network, whereby a dilation rate is increased for each encoding convolution performed to generate encoded image data;
  to decode the encoded image data using one or more convolutions in the dilated convolutional neural network, whereby dilation rate is decreased for each decoding convolution performed to generate decoded image data;
  to synthesize the decoded image data to construct a denoised output image corresponding to the noisy image; and
  to display the denoised output image on an image display device, the denoised output image having enhanced image quality compared to the noisy image.

* * * * *